(12) United States Patent
Armbruster et al.

(10) Patent No.: US 8,822,746 B2
(45) Date of Patent: Sep. 2, 2014

(54) ORDERED COBALT-ALUMINUM AND IRON-ALUMINUM INTERMETALLIC COMPOUNDS AS HYDROGENATION CATALYSTS

(75) Inventors: Marc Armbruster, Dresden (DE); Kirill Kovnir, Tallahassee, FL (US); Juri Grin, Dresden (DE); Robert Schlogl, Berlin (DE); Peter Gille, Munich (DE); Marc Heggen, Erkelenz (DE); Michael Feuerbacher, Duren (DE)

(73) Assignees: Max-Planck-Gesellschaft zur Foerderung der Wissenschaften E.V., Munich (DE); Ludwig-Maximilians-Universitaet Munich, Munich (DE); Forschungszentrum Juelich GmbH, Juelich (DE)

( * ) Notice: Subject to any disclaimer, the term of this patent is extended or adjusted under 35 U.S.C. 154(b) by 272 days.

(21) Appl. No.: 13/263,759

(22) PCT Filed: Mar. 22, 2010

(86) PCT No.: PCT/EP2010/053682
§ 371 (c)(1),
(2), (4) Date: Oct. 10, 2011

(87) PCT Pub. No.: WO2010/118929
PCT Pub. Date: Oct. 21, 2010

(65) Prior Publication Data
US 2012/0029254 A1 Feb. 2, 2012

Related U.S. Application Data

(60) Provisional application No. 61/269,093, filed on Jun. 19, 2009.

(30) Foreign Application Priority Data

Apr. 14, 2009 (EP) .................................. 09157875

(51) Int. Cl.
| | | |
|---|---|---|
| C07C 5/05 | (2006.01) |
| C07C 5/08 | (2006.01) |
| C07C 5/09 | (2006.01) |
| C07C 7/163 | (2006.01) |
| B01J 23/62 | (2006.01) |
| C30B 15/00 | (2006.01) |
| B01J 23/75 | (2006.01) |
| C30B 29/52 | (2006.01) |
| C10G 45/32 | (2006.01) |
| C22C 21/00 | (2006.01) |
| C22C 1/04 | (2006.01) |
| B22F 7/08 | (2006.01) |
| C30B 17/00 | (2006.01) |
| C30B 11/00 | (2006.01) |
| C07C 7/167 | (2006.01) |
| B01J 23/745 | (2006.01) |
| B01J 35/00 | (2006.01) |

(52) U.S. Cl.
CPC ................ *C10G 45/32* (2013.01); *C30B 15/00* (2013.01); *B22F 2998/00* (2013.01); *B01J 23/75* (2013.01); *C30B 29/52* (2013.01); *C22C 21/00* (2013.01); *C22C 1/0491* (2013.01); *B22F 7/08* (2013.01); *C30B 17/00* (2013.01); *C30B 11/00* (2013.01); *C07C 7/167* (2013.01); *B01J 23/745* (2013.01); *B01J 35/002* (2013.01); *C10G 2400/20* (2013.01)
USPC ........... 585/274; 585/250; 585/258; 585/259; 585/260; 585/275; 585/277; 502/325; 502/332; 502/336

(58) Field of Classification Search
CPC ............ C07C 5/05; C07C 7/167; C07C 5/09; C07C 7/163; C07C 5/08; B01J 23/62
USPC ................................................. 585/274, 250
See application file for complete search history.

(56) References Cited

FOREIGN PATENT DOCUMENTS

| | | |
|---|---|---|
| EP | 1834939 A1 * | 9/2007 |
| EP | 2039669 A1 | 3/2009 |
| JP | 46033006 | 11/1971 |
| JP | 59123539 | 7/1984 |
| WO | 2007104569 A1 | 9/2007 |
| WO | 2008145387 A2 | 12/2008 |

OTHER PUBLICATIONS

Komatsu et al, "Cobalt Intermetallic Compounds for Selective Hydrogenation of Acetylene"; Studies in Surface Science and Catalysis, Elsevier Science, vol. 101, Jan. 1, 1996; p. 1095-1104.

G. Gille et al; Cryst. Res. Technol. 43, No. 11, pp. 1161-1167, 2008.

Corresponding JP Office Action dated Nov. 12, 2013, with translation.

* cited by examiner

*Primary Examiner* — In Suk Bullock
*Assistant Examiner* — Youngsul Jeong (74) *Attorney, Agent, or Firm* — Harness, Dickey & Pierce, PLC

(57) ABSTRACT

The present invention relates to a process for the hydrogenation, in particular the selective hydrogenation of unsaturated hydrocarbon compounds, such as the selective hydrogenation of acetylene to ethylene, using a hydrogenation catalyst comprising an ordered intermetallic compound, namely an ordered cobalt-aluminum or iron-aluminum intermetallic compound. According to another aspect, the present invention relates to a catalyst comprising a support and at least one specific ordered cobalt-aluminum and/or iron-aluminum intermetallic compound supported thereon, as well as to the use of specific ordered intermetallic cobalt-aluminum and iron-aluminum intermetallic compounds as catalysts. The ordered cobalt-aluminum and iron-aluminum intermetallic compounds proved to be highly selective and long-term stable catalysts, e.g. in the selective hydrogenation of acetylene to ethylene in a large excess of ethylene.

12 Claims, 3 Drawing Sheets

ORDERED COBALT-ALUMINUM AND IRON-ALUMINUM INTERMETALLIC COMPOUNDS AS HYDROGENATION CATALYSTS

FIELD OF THE INVENTION

The present invention relates to a process for the hydrogenation, in particular the selective hydrogenation of unsaturated hydrocarbon compounds, using a hydrogenation catalyst comprising an ordered intermetallic compound, namely an ordered cobalt-aluminum or iron-aluminum intermetallic compound, to a catalyst comprising a support and at least one specific ordered cobalt-aluminum and/or iron-aluminum intermetallic compound supported thereon, as well as to the use of specific ordered intermetallic cobalt-aluminum and iron-aluminum intermetallic compounds as a catalyst.

BACKGROUND ART

Selective hydrogenations of unsaturated hydrocarbon compounds are of high industrial significance. The pyrolysis of naphtha for the production of ethene, propene, butanes, 1,3-butadiene and aromatic compounds is a key process in the modern petrochemical industry. For the nearly complete removal of alkynic compounds from the $C_2$, $C_3$ and $C_4$ cuts, selective hydrogenations are generally used.

For instance, the hydrogenation of acetylene is an important industrial process to remove traces of acetylene in the ethylene feed for the production of polyethylene. Because acetylene poisons the catalyst for the polymerisation of ethylene to polyethylene, the acetylene content in the ethylene feed has to be reduced to the low ppm range. Moreover, economic efficiency requires high selectivity of acetylene hydrogenation in the presence of an excess of ethylene to avoid the hydrogenation of a large fraction of the ethylene to ethane.

Palladium shows high activity for hydrogenation, in particular the hydrogenation of acetylene, but its selectivity is limited. In particular at high acetylene conversion, palladium will completely hydrogenate acetylene to ethane, convert ethylene to ethane, and form $C_4H_x$ and higher hydrocarbons by oligomerization reactions. In addition, deactivation of Pd during acetylene hydrogenation is caused by carbon and hydrocarbon deposits and necessitates frequent regeneration and/or exchange of the catalyst.

The $C_3$ cut (propylene) is generally purified by selective hydrogenation of propyne (methylacetylene) and propadiene (allene), and the obtained propylene may be further processed to polypropylene.

Another important selective hydrogenation in industry is the removal of traces of 1,3-butadiene from the $C_4$ fraction after the extractive separation thereof. $Pd/Al_2O_3$ catalysts are commonly used in this reaction. Furthermore, the selective hydrogenation of 1,5-cyclooctadiene, obtained by cyclic dimerization of 1,3-butadiene, to cyclooctene on $Pd/Al_2O_3$ and of benzene to cyclohexene on ruthenium catalysts are of importance.

For enhancing the selectivity of catalysts in selective hydrogenations, intermetallic compounds have recently attracted attention. For instance, WO 2007/104569 (claiming the priority of EP 1 834 939 A1), according to a general aspect, relates to selective hydrogenation processes using, as hydrogenation catalysts, specific ordered intermetallic compounds, which satisfy the so-called site isolation principle for the hydrogenation-active metals in the ordered intermetallic compound. The focus of the above WO publication is on ordered intermetallic compounds comprising palladium and/or platinum as hydrogenation-active metals. Concretely, PdGa, $Pd_3Ga_7$, $Pd_2Ga$, $Pd_2Ge$, PdZn and PtZn are tested in the selective hydrogenation of acetylene to ethylene, and the activity and selectivity of these catalysts is compared with conventional $Pd/Al_2O_3$ and $Pd_{20}Ag_{80}$ alloy catalysts. The scientific papers by J. Osswald et al. in Journal of Catalysis 258 (2008), pp. 210-218 and pp. 219-227 provide a similar teaching, while being limited to studies of the intermetallic compounds PdGa and $Pd_3Ga_7$.

High costs are connected with the use of both, palladium and platinum, so that industry has been interested in finding alternative hydrogenation catalysts that are inexpensive and nevertheless are highly active and selective, long-term stable catalysts.

The use of ordered intermetallic compounds as catalysts in a variety of different reactions is generally described in US 2004/0126267 A1 and WO 2004/012290 A2. However, these documents fail to disclose the application of this type of compounds to hydrogenations, let alone selective hydrogenations. In fact, the focus of these references is on their use in fuel cells. Moreover, they seemingly fail to mention ordered cobalt-aluminum or iron-aluminum intermetallic compounds.

U.S. Pat. No. 4,507,401 relates to supported intermetallic catalysts that are produced by a process which begins with the preparation of a supported Group VIII metal composition where the Group VIII metal includes iron, cobalt, nickel, ruthenium, rhodium, palladium, osmium, iridium, platinum or combinations of these metals. Then, the Group VIII containing support is contacted with a metal hydride or organometallic compound at a temperature sufficient to form an intermetallic compound wherein the metal hydride or organometallic compound contains at least one metal atom selected from the group consisting of silicon, germanium, aluminum, boron, gallium, indium and tin. In the working examples of the patent, supported nickel-silicon, nickel-germanium and nickel-aluminum intermetallic compounds are prepared. The supported catalysts are tested in the hydrogenolysis and dehydrogenation of cyclohexane.

EP 0 645 464 A2 is concerned with ultrafine particles of quasi-cristalline aluminum alloys, for instance of $Al_{65}Cu_{20}Fe_{15}$, $Al_{65}Cu_{20}Co_{15}$, $Al_{70}Ni_{15}CO_{15}$, $Al_{70}Pd_{17}Fe_{13}$ and $Al_{75}Pd_{15}CO_{10}$. The aluminum alloys are tested in methanol decomposition to yield hydrogen.

In P. A. Thiel, Annu. Rev. Phys. Chem. 2008, 59, pp. 129-52, d-Al—Ni—Co is assumed to have a good potential for service in the steam reforming of methanol.

H. Imamura et al. in The Journal of Physical Chemistry, Vol. 83, No. 15, 1979, pp. 2009-2012 describe the catalytic testing of CoAl, $CO_2Al_9$, FeAl and $Fe_3Al$ in methanation reactions.

L. V. Galaktionova et al. in Russian Journal of Physical Chemistry A, 2008, Vol. 82, No. 2, pp. 206-210 reports the conversion of $CO_2$ and $CH_4$ to CO and hydrogen using Fe-containing intermetallic compounds, e.g. $Fe_3Al$ and $Fe_2Al_5$.

In view of the above, it is an object of the present invention to provide a process for the hydrogenation of unsaturated hydrocarbon compounds, in particular of ethyne (acetylene) in admixture with a large excess of ethene (ethylene) to afford ethene, which overcomes the drawbacks in terms of activity and/or selectivity of the conventional hydrogenation catalysts as outlined above, and which furthermore is an inexpensive process in terms of costs of catalysts. It is another object to provide novel catalysts having the above beneficial properties in selective hydrogenation reactions, in particular in the selective hydrogenation of acetylene to afford ethylene when ethylene is present in an excessive amount.

SUMMARY OF THE INVENTION

The above objects are attained by a process for the hydrogenation of at least one unsaturated hydrocarbon compound using a hydrogenation catalyst comprising an ordered intermetallic compound, which is an ordered cobalt-aluminum intermetallic compound or an ordered iron-aluminum intermetallic compound.

According to another aspect, the present invention is concerned with a supported catalyst comprising a support and at least one ordered intermetallic compound supported thereon, which intermetallic compound is selected from the group consisting of CoAl, CoAl$_3$, CO$_2$Al$_5$, CO$_2$Al$_9$, o-CO$_4$Al$_{13}$, h-CO$_4$Al$_{13}$, m-CO$_4$Al$_{13}$, FeAl, FeAl$_2$, Fe$_3$Al, Fe$_2$Al$_5$ and Fe$_4$Al$_{13}$. In this specification, "o-CO$_4$Al$_{13}$" means orthorhombic CO$_4$Al$_{13}$, "h-CO$_4$Al$_{13}$" means hexagonal CO$_4$Al$_{13}$, and "m-CO$_4$Al$_{13}$" denotes monoclinic CO$_4$Al$_{13}$.

According to still another aspect, the present invention relates to the use of an ordered intermetallic compound, which is CoAl$_3$, CO$_2$Al$_5$, o-CO$_4$Al$_{13}$, h-CO$_4$Al$_{13}$, m-CO$_4$Al$_{13}$, FeAl$_2$ or Fe$_4$Al$_{13}$ as a catalyst.

Preferred embodiments of the present invention are subject of the dependent claims.

DETAILED DESCRIPTION OF THE INVENTION

The benefits of the hydrogenation process of the present invention can be achieved preferentially if the hydrogenation proceeds selectively.

Everyone active in the field of hydrogenation catalysis is familiar with the term "selective hydrogenation". Generally, a chemical reaction is referred to as being selective if it converts preferentially one of several functional groups which are present in the molecules of the reaction mixture, whereas the remaining functional groups of this type react to a significantly lower degree, i.e. they do hardly react in the case of highly selective reactions. Differently stated, a hydrogenation is selective if it selects a certain hydrogenation reaction (or certain hydrogenation reactions) from the various hydrogenation reactions which are possible in the reaction mixture. Consequently, the term "selective hydrogenation" as it is used herein covers e.g., the following situations: (1) some of the unsaturations (e.g. double and/or triple bonds) of the unsaturated hydrocarbon compound to be reacted are hydrogenated with preference whereas the other unsaturations react to a significantly lower degree, and (2) in the case that one or more unsaturations of the unsaturated hydrocarbon compound to be reacted can be hydrogenated twice (e.g. triple bonds), they are hydrogenated with preference only once, and the 2nd reaction step is hardly observed. For the purpose of the present invention, a hydrogenation is referred to as selective if the molar ratio of the desired target compound to the undesired target compound(s) is larger than 1:1, preferably more than 2:1, more preferably more than 5:1, most preferably 10:1, and especially >10:1.

A typical example of situation (1) is the hydrogenation of an alkadiene to afford mainly, preferably almost exclusively, the corresponding alkene without substantial reaction of the alkene to the corresponding alkane. Situation (2) may be exemplified by the reaction of an alkyne to give mainly the corresponding alkene, whereas the consecutive reaction of the alkene to afford the alkane hardly takes place. As will be appreciated from the above, the two situations are not mutually exclusive. That means, both of the above situations may exist in the selective hydrogenation of a specific molecule. In the case of the acetylene reaction in a large excess of ethylene which corresponds to situation (2), it is important that the ethylene, in spite of its large concentration, is hardly converted to ethane.

Examples of selective hydrogenations have been described in the Background Art section of the present specification.

The unsaturated hydrocarbon compound used in the hydrogenation process of the present invention is not limited in kind as long as this contains one or more unsaturations susceptible to hydrogenation, and preferably it poses a selectivity problem as outlined above. As suggested by the name, the unsaturated hydrocarbon compound comprises hydrogen and carbon atoms. For example, the unsaturated hydrocarbon compound may be an unsaturated carbonyl compound, e.g. a compound having both a carbonyl moiety and a carbon-carbon double bond in the molecule. However, the unsaturated hydrocarbon compound preferably contains, as unsaturations susceptible to hydrogenation, carbon-carbon double and/or carbon-carbon triple bonds, and is free from further unsaturations susceptible to hydrogenation, i.e. hydrogenable group(s). According to a more preferred embodiment, the unsaturated hydrocarbon compound is selected from the group consisting of alkadienes, alkatrienes and alkapolyenes; alkynes, dialkynes, trialkynes and polyalkynes; and aromatic compounds. The alkadienes, alkatrienes and alkapolyenes, and the alkynes, dialkynes, trialkynes and polyalkynes cover both, alicyclic and cyclic compounds. Still more preferably, the unsaturated hydrocarbon compound is selected from the group of alkadienes, cycloalkadienes, alkynes and benzene.

The alkadiene may be 1,3-butadiene, which will be converted by way of the selective hydrogenation of the present invention, mainly to 1-butene, without being fully hydrogenated to butane to a significant degree. The cycloalkadiene is, for example, 1,5-cyclooctadiene which will afford upon the selective hydrogenation of the invention cyclooctene, while cyclooctane resulting from the full hydrogenation is a minor product. The selective hydrogenation of benzene will afford cyclohexene with minor amounts of cyclohexadiene and cyclohexane. An example of a selective hydrogenation of a triple bond in the presence of a double bond is the purification of 1,3-butadiene by hydrogenation of vinyl acetylene present in the mixture. Still another example of a selective hydrogenation is the reaction of nitrobenzene to aniline.

According to a particularly preferred embodiment, the unsaturated hydrocarbon compound is an alkyne, in particular an alkyne having 1 to 4, especially 1 or 2 carbon-carbon triple bonds. Most preferably, the alkyne is ethyne (acetylene). Through the selective hydrogenation process of the invention, ethyne will predominantly be converted to ethene (ethylene) while the hydrogenation of ethene to afford ethane is negligible. This is even so when the selective hydrogenation of ethyne is carried out under reaction conditions where ethyne is present in admixture with an excess of ethene in relation to ethyne, which is a particularly preferred embodiment of the selective ethyne hydrogenation according to the present invention. Most preferably, ethene is present in the reaction mixture to be hydrogenated in a large excess in relation to ethyne. The ethyne to ethene weight ratio in the starting mixture of the selective ethyne hydrogenation of the invention is preferably 1:10 to 1:10$^6$, more preferably 1:50 to 1:10$^3$. In industrial processes, the ethene to ethyne weight ratio in the mixture obtained after the selective hydrogenation is typically as large as >10$^6$.

The selective hydrogenation of phenyl acetylene to styrene in excess of styrene is another example of a selective hydrogenation. As will be appreciated, that reaction is the polystyrene counterpart of the selective acetylene hydrogenation in excess of ethylene in the feed used for the preparation of polyethylene.

The skilled person in the field of hydrogenation catalysis will readily select and optimise the reaction parameters for a certain selective hydrogenation reaction. To provide some guidance, the temperature range of industrial selective hydrogenations may be in the range of 10° to 300° C., preferably 20° to 250° C., most preferably 30° to 200° C. The pressure may be 1 to 100 bar, preferably 2 to 75 bar, most preferably 5 to 50 bar. For more details, reference is made to WO 03/106020.

As used herein, the term "ordered intermetallic compound" refers to a chemical compound of two or more metallic elements, which adopts an ordered crystal structure that preferably differs from those of the constituent metals. In the ordered crystal structure, substantially all unit cells include the same arrangement of metal atoms. As meant herein, the ordered cobalt-aluminum intermetallic compound (occasionally abbreviated as "Co—Al-IMC", hereinafter) preferably comprises predominantly cobalt and aluminum atoms. Similarly, the ordered iron-aluminum intermetallic compound (occasionally abbreviated as "Fe—Al-IMC", hereinafter) preferably comprises predominantly iron and aluminum atoms. The expression "comprises predominantly" as used herein is intended to account for the situation, that there may be third, fourth, fifth, sixth etc. types of metals other than cobalt and aluminum in Co—Al-IMC, and other than iron and aluminum in Fe—Al-IMC. As will be appreciated, ordered intermetallic compounds comprising such third, fourth, fifth, sixth etc. types of metals can also be referred to as ternary, quaternary and multinary ordered intermetallic compounds, respectively. In this case, the total amount of cobalt and aluminum in Co—Al-IMCs, and the total amount of iron and aluminum in Fe—Al-IMCs is preferably more than 50 mol %, and this is implied by the above expression "comprises predominantly". According to a preferred embodiment, the total amount of cobalt and aluminum (in Co—Al-IMCs) and the total amount of iron and aluminum (in the case of Fe—Al-IMCs) is at least 80 mol % in ternary, quaternary or multinary ordered intermetallic compounds in accordance with the present invention.

According to a preferred embodiment, the ordered intermetallic compounds for use in the present invention are binary compounds, i.e. those substantially consisting of cobalt and aluminum (in the case of binary Co—Al-IMCs) or of iron and aluminum (in the case of binary Fe—Al-IMCs). Thereby, the expression "substantially consisting of" is intended to account for the presence of metallic impurities (i.e. different from cobalt or aluminum in the case of Co—Al-IMCs, and different from iron and aluminum in the case of Fe—Al-IMCs), that may originate from impurities in the starting materials or the synthesis procedure, in the binary ordered intermetallic compounds for use in the present invention. Thereby, the amount of metallic impurities within the binary ordered intermetallic compound is preferably •100 ppm.

The catalyst for use in the invention may be an unsupported or a supported catalyst.

If it is an unsupported catalyst, the ordered intermetallic compound, which is preferably a single-phase material, may make up at least 90%, preferably at least 95%, more preferably at least 99% of the catalyst. The balance to 100% may, for example, consist of volumes of a non-ordered intermetallic compound which may e.g., be due to the preparation method of the ordered intermetallic compound. Most preferably, the catalyst for use in the selective hydrogenation process of the invention consists entirely of the Co—Al-IMCs and/or Fe—Al-IMCs as defined above, especially single-phase materials of these IMCs.

It will be appreciated that defects which usually cannot be completely avoided in a real crystal may be present in the ordered intermetallic compound. Such defects can cause a small number of unit cells in the ordered intermetallic compound to have an arrangement of metal atoms different from the majority of the unit cells. Defect types include for example vacancies, interstitials, atom substitutions and anti-site defects.

Crystal imperfections due to the presence of defects may lead to a certain homogeneity range of the ordered intermetallic compounds. Therefore, the formulae used in the present specification (such as e.g. Fe$_4$Al$_{13}$), which refer to the ideal crystal structure, are meant to refer to the range of a single phase of the particular composition represented by the formula in the phase diagram of the metals forming the ordered intermetallic compound. As will be appreciated from the above, the stoichiometric ratio of the metals forming the ordered intermetallic compound as used in the formula may vary up and down, as long as it is within the range of the single phase of the respective ordered intermetallic compound in the phase diagram.

The ordered intermetallic compounds within the meaning of the present invention are to be distinguished from metal alloys and metal solid solutions. Alloys and solid solutions do not have an ordered atomic structure, as described above. Metal atoms are arranged randomly on the crystallographic sites in unit cells of alloys and solid solutions.

Ordered intermetallic compounds also generally have a more stable atomic arrangement in comparison to alloys and solid solutions. This results in an enhanced lifetime of the catalyst under reaction conditions. In alloys and solid solutions, atoms are prone to migration with an associated reduction of catalytic performance.

In the ordered intermetallic compounds according to the present invention, in particular the binary Co—Al-IMCs and binary Fe—Al-IMCs, the molar ratio of cobalt and aluminum and iron and aluminum, respectively, is preferably in the range 20:1 to 1:20.

The specific binary ordered Co—Al-IMC for use in the hydrogenation process of the present invention is preferably selected from the group consisting of CoAl, CoAl$_3$, Co$_2$Al$_5$, Co$_2$Al$_9$, o-Co$_4$Al$_{13}$, h-Co$_4$Al$_{13}$ and m-Co$_4$Al$_{13}$, and the specific ordered Fe—Al-IMC is preferably selected from the group consisting of FeAl, FeAl$_2$, Fe$_3$Al, Fe$_2$Al$_5$ and Fe$_4$Al$_{13}$.

The more preferred group of (binary) ordered intermetallic compounds for use in the present invention comprises CoAl, o-Co$_4$Al$_{13}$, h-Co$_4$Al$_{13}$, m-Co$_4$Al$_{13}$, FeAl and Fe$_4$Al$_{13}$. These specific intermetallic compounds may be used in the selective hydrogenation of any unsaturated hydrocarbon, in particular, in the following reactions: (cyclo)alkadiene→(cyclo)alkene and alkyne→alkene (in particular, ethyne→ethene).

In a particular preferred embodiment of the present invention, acetylene that is present in admixture with ethene is hydrogenated using as a hydrogenation catalyst a single-phase ordered Co—Al-IMC or Fe—Al-IMC, which is preferably single-phase CoAl, FeAl, o-$Co_4Al_{13}$, h-$Co_4Al_{13}$, m-$Co_4Al_{13}$ or $Fe_4Al_{13}$, more preferably single-phase o-$Co_4Al_{13}$, h-$Co_4Al_{13}$, m-$Co_4Al_{13}$ or $Fe_4Al_{13}$.

It was surprisingly found by the present inventors that ordered intermetallic cobalt-aluminum and iron-aluminum compounds as recited in claim 1 offer distinct advantages in selective hydrogenations, e.g., over the supported monometallic catalysts of the prior art, such as supported palladium, platinum and rhodium catalysts, and over alloyed or promoted palladium catalysts, in terms of selectivity to the desired product. Without wishing to be bound by theory, the enhanced selectivity has been attributed to the electronic modification of active sites, i.e. cobalt and iron, leading to altered adsorption of e.g. acetylene and ethylene on the surface compared to the monometallic catalysts of the prior art (electronic effect). Furthermore, a limited hydrogen concentration on the surface and the absence of hydride phases under the actual reaction conditions is considered to contribute to the high selectivity (kinetic effect). The absence of hydride phases under the reaction conditions in the selective hydrogenation of acetylene has been verified by experiment using Prompt Gamma Activation Analysis (PGAA). More details of this method will be given in the experimental section of this description.

As the present inventors found, the specific binary ordered intermetallic compounds FeAl, CoAl, $Fe_4Al_{13}$ and o-$Co_4Al_{13}$ are particularly selective hydrogenation catalysts, in particular in the selective hydrogenation of acetylene to ethylene. Moreover, the activity of $Fe_4Al_{13}$ and o-$Co_4Al_{13}$ was shown to be superior to the activity of FeAl and CoAl. Consequently, $Fe_4Al_{13}$ and o-$Co_4Al_{13}$ are the most preferred ordered intermetallic compounds for use in the process of the present invention. The present invention is also concerned with the general use of these particular ordered intermetallic compounds as catalysts.

The ordered Co—Al-IMCs and Fe—Al-IMCs of the present invention, in particular those individually mentioned in this specification were shown to exhibit excellent structural stability under typical reaction conditions in hydrogenations. In fact, these ordered intermetallic compounds, in particular $Fe_4Al_{13}$ and o-$Co_4Al_{13}$ proved to be stable in air and $H_2$/He up to at least 600° C. The excellent structural stability has been ascribed to partly covalent bonding in the structure. Owing to their outstanding stability, the ordered Co—Al-IMCs and Fe—Al-IMCs of the present invention, in particular $Fe_4Al_{13}$ and o-$Co_4Al_{13}$, are of course also promising candidates as catalysts for further types of reactions.

The ordered intermetallic compounds for use in the present invention can be readily synthesized by one of average skill in the art of solid state chemistry in due consideration of the phase diagrams of the ordered Co—Al-IMC or Fe—Al-IMC as published in the literature. The principles of how phase diagrams are to be interpreted are summarized by J. L. Meijering in Philips Technische Rundschau 26, 1965, pp. 114-129 and pp. 159-168, and in Philips Technische Rundschau 27, 1966, pp. 224-239. Dependent on the phase diagram of the intermetallic system, simple melting of appropriate amounts of the constituent metals with subsequent cooling may be sufficient. In some cases, supercooling may be necessary to reach the region of the phase diagram corresponding to the desired ordered intermetallic compound. The as-made ingots of ordered intermetallic compounds may be purified, e.g. by re-melting or other conventional purification methods as desired. The identity of the material obtained can be verified e.g. by X-ray diffraction.

In the case of CoAl and FeAl the melting of the respective elements in a molar ratio of 1:1 in a suitable furnace equipped with a water cooled copper heart under inert atmosphere proved sufficient. The obtained ingots could be purified by re-melting.

The preparation of some ordered Co—Al-IMCs or Fe—Al-IMCs may involve annealing steps, e.g., where the respective compound does not crystallize from the melt. To give an example, this proved beneficial for obtaining single phase FeAl. Looking at the phase diagram of the respective intermetallic system, the skilled person will conclude where annealing is necessary to achieve the thermodynamic equilibrium of the sample so that the thermodynamically most stable modification is formed. The annealing is preferably carried out for an amount of time as large, and at a temperature as high as possible.

For the preparation of $Fe_4Al_{13}$ and o-$Co_4Al_{13}$ single crystals, P. Gille and B. Bauer describe in Cryst. Res. Technol. 43, No. 11, pp. 1161-1167 (2008) a Czochralski method using Al-rich starting melts. This method is advantageous for obtaining large single crystals of these materials and is as such used with preference for preparing $Fe_4Al_{13}$ or o-$Co_4Al_{13}$ for use in the present invention. The method described in the above paper is not limited to the Czochralski method. The Bridgman, flux growth and top seeded solution growth (TSSG) methods can likewise be used in place of the Czochralski method. This is because, thermodynamically, there is no difference between all of these methods. Decisive is the fact that the crystal growth is started from Al-rich melts. As can be seen from the Al-rich parts of the phase diagrams that are shown on page 1164 of the above paper from P. Gille and B. Bauer, large single crystals of orthorhombic $Co_4Al_{13}$ or of monoclinic $Fe_4Al_{13}$ can be obtained by the method.

As mentioned earlier, the ordered intermetallic compound for use in the process of the invention may be used in the as-synthesized form as an unsupported catalyst. In this case, the specific surface area (BET method, $N_2$ adsorption, for more details see the Examples) is typically in the range of 0.001 to 0.1 $m^2$/g. To increase the catalyst surface area, so as to enhance the activity of the catalyst, it proved beneficial to comminute (e.g. pulverize) the ordered intermetallic compound. For example, the ingot of the ordered intermetallic compound obtained from the constituent metals as explained above may be comminuted with an associated increased catalyst activity. The powder form is a preferred embodiment of the comminuted ordered intermetallic compound for use in the present invention. The means to be used for comminuting (e.g. pulverizing) the ordered intermetallic compound are not limited in kind, and may be ball mills, swing mills, cryo mills, planetary mills, etc. optionally in an argon atmosphere. In the alternative, the ordered intermetallic compounds may be ground by hand, e.g. using a mortar. The above combination treatments result in a specific surface area of the ordered intermetallic compound which is typically in the range of 0.05 to 20 $m^2$/g, preferably 0.1 to 10 $m^2$/g, and most preferably of 0.2 to 5 $m^2$/g.

The ordered Co—Al-IMCs and/or ordered Fe—Al-IMCs may also be used in the hydrogenation process of the invention in the form of a mixture of a powder thereof with an inert material, e.g. silica, alumina, titania, zirconia, zeolites, active carbon, talc, kaolin, boron nitride and clays such as described in EP 2 039 669 A1. These mixtures differ from supported catalysts to be described below in that the ordered intermetallic compound and the inert material are unfixed and can flow freely, so that the mixture can be separated, e.g. by flotation, into the inert material(s) and the ordered intermetallic compound(s). This is of course not possible for a supported catalyst. The above mixture of powdered ordered intermetallic compound and inert support(s) is preferably a dry mixture, especially a dry mixture of powdered ordered intermetallic compound and powdered inert support(s).

The surface area of the hydrogenation catalyst for use in the process of the present invention may also be increased by using the catalyst in supported form. Accordingly, the present invention, according to another aspect, is concerned with a supported catalyst comprising a (binary) intermetallic compound selected from the group consisting of CoAl, $CoAl_3$, $Co_2Al_5$, $Co_2Al_9$, $o\text{-}Co_4Al_{13}$, $h\text{-}Co_4Al_{13}$, $m\text{-}Co_4Al_{13}$, FeAl, $FeAl_2$, $Fe_3Al$, $Fe_2Al_5$ and $Fe_4Al_{13}$, preferably $Fe_4Al_{13}$ and $o\text{-}Co_4Al_{13}$, or mixtures thereof, provided on a support. Suitable supports are those commonly used in catalysis, e.g. compounds having a high surface area, such as active carbon, alumina, silica, silicates, etc. For preparing the supported catalyst, powders of the binary intermetallic compounds can for instance be dispersed in a suitable liquid, such as $C_{1-4}$ alcohols or an inert solvent, preferably an aprotic and polar solvent, such as tetrahydrofurane (THF) or propylene carbonate, to form a slurry of the powders. Then, the support is impregnated with the slurry, dried, and heated in a reductive atmosphere, for instance at a temperature of 200 to 600° C., preferably 300 to 500° C. so as to fix the intermetallic compound(s) to the support, thus forming a supported catalyst.

Figure 3:
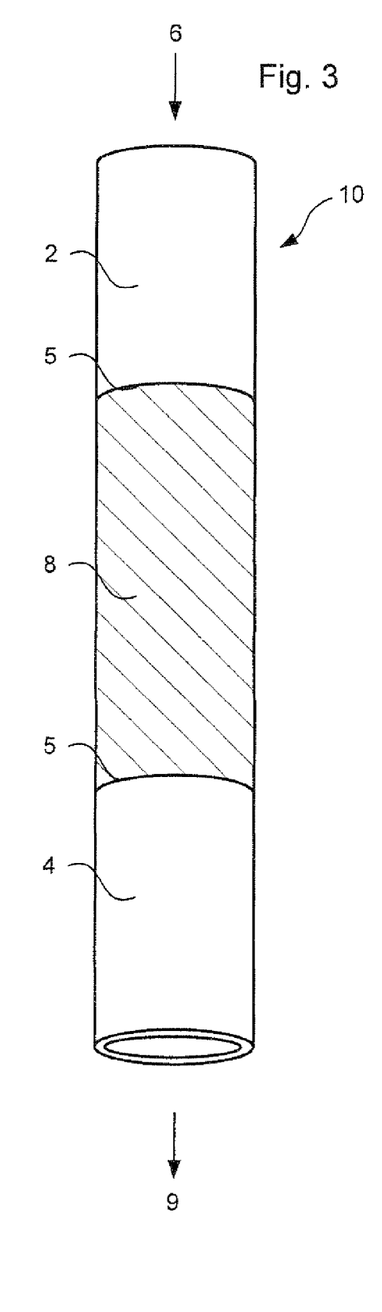
FIG. 3 is a schematic drawing showing a tubular reactor, a tube segment of which is composed of an ordered intermetallic compound in accordance with the present invention.
Figure 4:
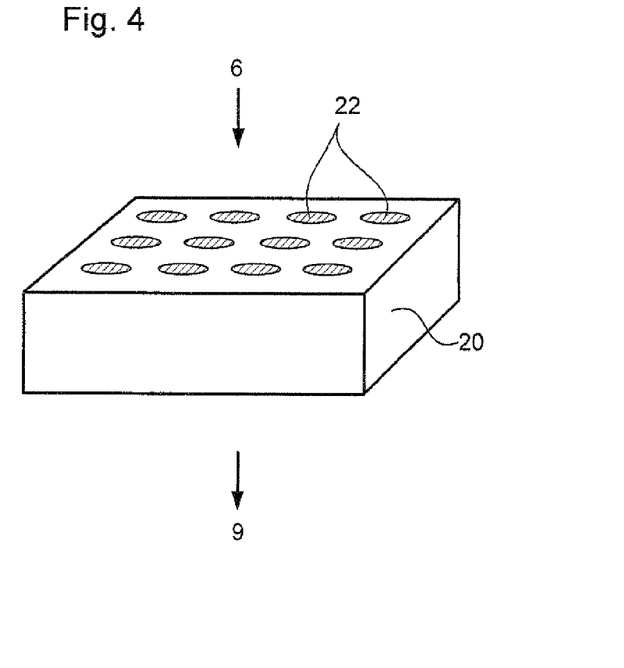
FIG. 4 is a schematic drawing showing a monolithic body composed of an ordered intermetallic compound in accordance with the present invention.

As explained above, the ordered intermetallic compounds for use in the present invention may be obtained as a result of their preparation methods in the form of ingots. In spite of the brittleness of some of them, they can be brought into a desirable form e.g. by spark machining. Consequently, the ingot, e.g. of CoAl, FeAl, $Fe_4Al_{13}$, $o\text{-}Co_4Al_{13}$, $h\text{-}Co_4Al_{13}$ or $m\text{-}Co_4Al_{13}$ can be formed, e.g. by way of spark machining, into a monolith, such as a tube segment of a tubular reactor. This is illustrated in FIG. 3. The figure shows a tubular reactor 10 composed of an inlet tube section 2 and an outlet tube section 4, which are made of material that is non-reactive with the reaction mixture 6 entering the tubular reactor 10. For instance, tube sections 2 and 4 can be made of stainless steel or glass. Tube segment 8 is made of the ordered intermetallic compound of the invention that has been brought e.g. by way of spark machining, into the form of that tube segment. Within tube segment 8, the reaction mixture 6 is converted through the activity of the ordered intermetallic compound as a catalyst, in particular hydrogenation catalyst, to the product mixture 9. As will be appreciated, the vertical arrows in FIG. 3 show the flow direction of the reaction mixture 6 that is converted within the tube section 8 to the product mixture 9. In the tubular reactor 10, the tube segments 2, 4 and 8 may be connected at the positions 5 e.g. with flanges or by bonding. The tube segment 8 represents a monolith composed or consisting of the ordered intermetallic compound. In FIG. 4, the monolith of the ordered intermetallic compound is a brick-like monolith 20 that is provided with several holes 22. Like in FIG. 3, the reaction mixture 6 flows through the holes 22 in the direction of the arrow, and is converted to the products through the catalytic action of the ordered intermetallic compound forming the brick-like monolith 20 to give the product mixture 9. As will be understood from the above, the "monolith", in which form the ordered intermetallic compound may be used in the present invention, means a one-piece part made of the ordered intermetallic compound.

According to a specific embodiment of the present invention, the ordered intermetallic compound, which is $Fe_4Al_{13}$ or $o\text{-}Co_4Al_{13}$, is used as a catalyst in the form of a monolith. Evidently, the consumption of material for the preparation of such monoliths is large. In view of the low costs of the metals constituting the ordered intermetallic compounds of the invention, in particular the binary ones, this is however of no major concern.

The following Examples are given for illustration of the invention and must not be construed in a limiting sense.

EXAMPLES

Preparation of Catalysts

For the synthesis of CoAl, Co-foil (Alfa Aesar 99.995%) and Al-rod (ChemPur 99.999%) were mixed in a molar ratio of 1:1 and molten in an arc furncace (35 A) with water cooled copper heart under inert argon atmosphere. The ingot formed after cooling was re-molten three times in the same furnace. Subsequent powder X-ray diffraction of the sample analysis revealed a single phase sample of CoAl (CsCl-Structure).

For the synthesis of FeAl, Fe-foil (Alfa Aesar 99.995%) and Al-rod (ChemPur 99.999%) were mixed in a molar ratio of 1:1 and molten in an arc furnace (36 A) with water cooled copper heart under inert argon atmosphere. The ingot formed after cooling was re-molten three times in the same furnace. Subsequently, the sample was enclosed in an evacuated quartz glass tube and annealed at 900° C. for 10 days. Powder X-ray diffraction analysis of the sample resulted in the detection of single phase FeAl (CsCl-Structure).

Ingots of $Fe_4Al_{13}$ and $o\text{-}Co_4Al_{13}$ were obtained by the Czochralski method in accordance with G. Gille and B. Bauer, Cryst. Res. Technol. 43, No. 11, pp. 1161-1167 (2008). In the case of $Fe_4Al_{13}$, powder X-ray diffraction analyses of the sample resulted in the detection of a single phase of monoclinic $Fe_4Al_{13}$, and in the case of $Co_4Al_{13}$ in the detection of single phase orthorhombic $Co_4Al_{13}$.

To elucidate the thermal stability of $Fe_4Al_{13}$ and $o\text{-}Co_4Al_{13}$, samples of them were subjected to DTA/TG measurements (i.e. coupled differential thermal analysis and thermogravimetry). The measurements were performed on a Netzsch STA 449 C DSC/TG instrument using 30 mg of sample at a heating rate of 6 K/min in the indicated atmospheres. As a result, the oxidation of $Fe_4Al_{13}$ in air started at only 750° C., and of $Co_4Al_{13}$ at only 600° C. DTA/TG/MS, i.e. combined differential thermal analysis, thermogravimetry and mass spectrometry using the above Netzsch STA 449 C DSC/TG instrument (sample mass: 30 mg; heating rate: 6 K/min), and continuously analyzing the exhaust gas stream by a Pfeiffer Omnistar mass spectrometer, in 50% $H_2$/He gave the following results. For both materials, there was no weight gain up to 400° C. and then a small gain up to 600° C., and there was no loss of the constituent metals up to 600° C. The above high stability of the materials could be confirmed by in-situ high-pressure XPS experiments at beamline U49/2-PGM1 at BESSY (Berlin, Germany). For details of the set-up in these XPS experiments, reference can be made to H. Bluhm et al, J. Phys. Chem. B 108 (2004) 14340. Moreover, $Fe_4Al_{13}$ and $Co_4Al_{13}$ were subjected to Prompt Gamma Activation Analysis (PGAA) under the following conditions: 473 K, 2 ml/min propyne, 10 ml/min ethylene, 14 ml/min hydrogen; no mixing of sample with inert BN. Z. Révay et al. in Analytical Chemistry, Vol. 80, No. 15, Aug. 1, 2008 provide more details on the set-up in PGAA. No hydride formation was detected by PGAA under the above conditions.

Prior to the catalytic tests to be described below, the single crystals obtained in the above methods were comminuted under an inert argon atmosphere. Specifically, the samples were divided in a mortar (agate mortar) into small fragments by hand, which fragments were then further comminuted in the mortar to result in fine powder. Due to the brittleness of the materials, the particle size was in the range of 20 μm.

Catalytic Measurements

Catalytic investigations were performed in a plug flow reactor consisting of a quartz tube with a length of 300 mm, an inside diameter of 7 mm and equipped with a sintered glass frit to support the catalyst bed. For temperature control, a thermocouple was located next to the heating wire wound around the reactor. A second thermocouple was placed inside the reactor to measure the temperature of the catalyst bed. The reactant gases were mixed with Bronkhorst mass flow controllers (total flow 30 ml/min). A Varian CP 4900 Micro gas chromatograph (GC) and was used for effluent gas analysis. The Varian MicroGC contains three modules, each with an individual column and a thermal conductivity detector. Hydrogen and helium of the feed gas, and possible oxygen and nitrogen impurities because of leaks in the set-up were separated on a molsieve column. Acetylene, ethylene, and ethane were separated on an alumina column. The total concentration of $C_4$ hydrocarbons (1-butene, 1,3-butadiene, n-butane, trans and cis-2-butene) was determined using a siloxane (dimethylpolysiloxane) column. Higher hydrocarbons were also separated on the siloxan column but not further quantified because of the presence of many different $C_6$ and $C_8$ hydrocarbons and their low total concentration (less than 0.1% of absolute product stream concentration). Argon (6.0) and helium (6.0) were used as carrier gases for the molsieve column and for the other columns, respectively. A measurement cycle including stabilization, sampling, injection, and separation took between 4 and 5 minutes.

Acetylene hydrogenation experiments were carried out under the condition of 0.5% acetylene (Praxair), 5% hydrogen (Air Liquide), and 50% ethylene (Westfalen Gas) in helium (Praxair) (i.e. 44.5% He).

Activity and selectivity of the materials in the hydrogenation of acetylene were measured by temperature-programmed and by isothermal experiments. The experiments were performed at 473 K in the isothermal mode. The conversion rate was calculated using the following equation:

$$Conv = \frac{(C_{bypass} - C_x)}{C_{bypass}}$$

where $C_x$ is the acetylene concentration in the product stream and $C_{bypass}$ is the acetylene concentration in the feed before the reaction. The selectivity was calculated from the following equation, with $C_{bypass}$ being the acetylene concentration before the reactor and $C_x$ the acetylene concentration after the reactor:

$$Sel = \frac{(C_{bypass} - C_x)}{C_{bypass} - C_x + C_{ethane} + 2xC_{C4Hx}}$$

Calculation of the selectivity assumes that acetylene is only hydrogenated to ethylene, which may be further hydrogenated to ethane. The amount of $C_4$ hydrocarbons and carbon deposits formed was supposed to be negligible. In addition to hydrogenation of acetylene to ethane, ethylene from feed may be hydrogenated to ethane, which is included in the selectivity equation. In order to measure selectivity in acetylene hydrogenation at the same conversion, different amounts of catalysts were used according to their specific activity determined in a previous experiment.

Activity of the samples was calculated using following equation:

$$Act = \frac{ConvC_{feed}C_{exp}}{m_{cat}}$$

where Conv is the calculated acetylene conversion, $C_{feed}$ is the concentration of acetylene in feed, i.e. 0.5%, $m_{cat}$ the amount of used catalyst in g and constant $C_{exp}$ is 1.904 g/h and contains experimental parameters like total gas flow (30 ml), temperature (300 K) and pressure (1013 mbar) and is based on the perfect gas model.

The samples were diluted with 50-150 mg inert boron nitride (hexagonal, 99.5%, 325 mesh, Aldrich). A commercial Pd on alumina catalyst (5 wt % Pd, Aldrich) was used as a reference. Additionally, an unsupported palladium silver alloy was used as a benchmark catalyst. The Pd—Ag alloy ($Pd_{20.28}Ag_{79.72}$, referred to as $Pd_{20}Ag_{80}$ in the following) was prepared by melting the corresponding physical mixture of the elements 1.20405 g Ag (99.995% ChemPur) and 0.30348 g Pd (99.95% ChemPur) three times in an arc melter under argon.

Subsequently, the regulus obtained was enclosed in an evacuated quartz glass ampoule and heated at 800° C. for six days. After the heat treatment, the regulus was powdered and phase purity of the Pd—Ag alloy obtained was confirmed by X-ray powder diffraction.

Examples 1 to 4, and Comparative Examples 1 and 2

The activity, selectivity, and long-term stability of ordered Co—Al-IMCs and Fe—Al-IMCs ($Fe_4Al_{13}$ in Example 1; o-$CO_4Al_{13}$ in Example 2; FeAl in Example 3 and CoAl in Example 4) in the selective hydrogenation of acetylene in an excess of ethylene was determined under the conditions outlined in the preceding section, and compared to the catalytic performance of Pd/$Al_2O_3$ (Comparative Example 1) and a $Pd_{20}Ag_{80}$ alloy (Comparative Example 2).

Isothermal catalysis experiments were performed by heating the ordered intermetallic compounds and the reference materials in the amounts indicated in Table 1 below (cf. the column denoted catalyst mass) in helium to a reaction temperature of 473 K followed by switching to the ethylene-rich feed.

Figure 1:
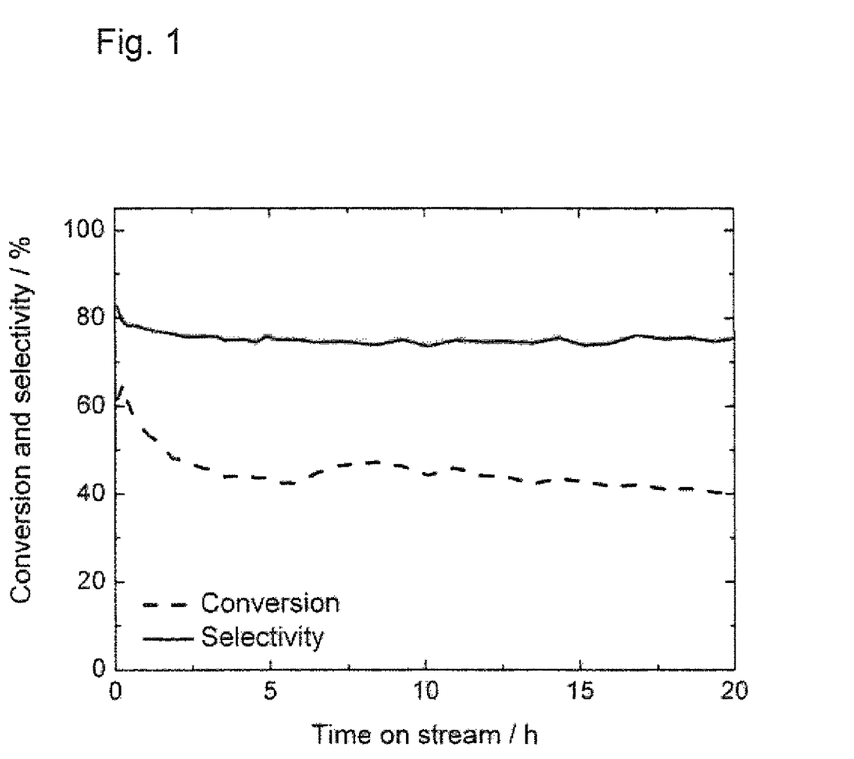
FIG. 1 shows the conversion and selectivity of Fe$_4$Al$_{13}$ (158 mg) in the hydrogenation of acetylene in admixture with an excess of ethylene at 473 K.
Figure 2:
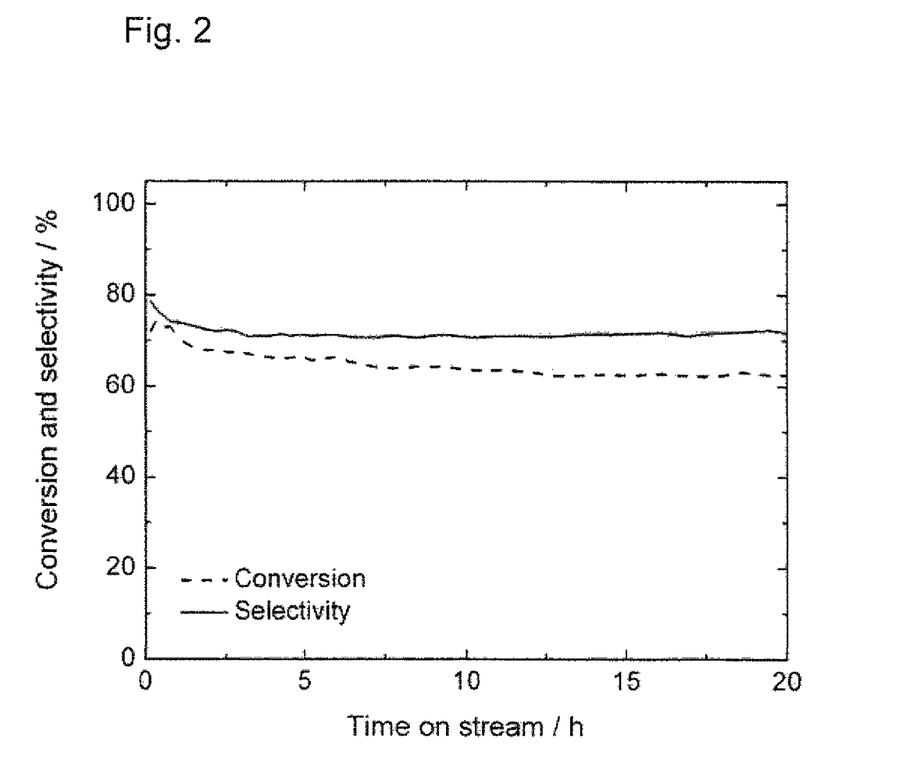
FIG. 2 shows the conversion and selectivity of o-CO$_4$Al$_{13}$ (150 mg) in the hydrogenation of acetylene in admixture with an excess of ethylene at 473 K.

The acetylene conversion and the corresponding selectivity using $Fe_4Al_{13}$ powder are shown in FIG. 1, and the corresponding data obtained using o-$CO_4Al_{13}$ powder are plotted in FIG. 2. As can be seen from the figures, both ordered intermetallic compounds reached an almost constant acetylene conversion after 2-3 hours on stream with only a slight decay until 20 h on stream, which time is used herein as a reference point for the comparison with conventional catalysts. The selectivity of both ordered intermetallic compounds was as high as 75% ($Fe_4Al_{13}$) and 71% (o-$CO_4Al_{13}$) after 20 h on stream. Consequently, in view of FIGS. 1 and 2, the ordered intermetallic compounds tested have a high long-time stable selectivity of above 70%. As will be shown below, this is significantly above the selectivity obtained with the (much more expensive) conventional catalysts $Pd_{20}Ag_{80}$ and Pd/$Al_2O_3$.

The results of the catalytic testing are summarized in Table 1 below, which also shows for comparison data obtained for the conventional catalysts $Pd_{20}Ag_{80}$ and $Pd/Al_2O_3$.

TABLE 1

Acetylene conversion and selectivity after 20 h in an excess of ethylene at 473 K using ordered intermetallic compounds in accordance with the invention and conventional catalysts.

| Experiment | Catalyst material | Catalyst mass [mg] | Acetylene conversion % | Selectivity % | Activity[1] [$g/g_{cat} \cdot h$] |
|---|---|---|---|---|---|
| Example 1 | $Fe_4Al_{13}$ | 158 | 40 | 75 | 0.0265 |
| Example 2 | $o\text{-}Co_4Al_{13}$ | 150 | 62 | 71 | 0.0432 |
| Example 3 | FeAl | 650 | 20 | 70 | 0.0032 |
| Example 4 | CoAl | 810 | 21 | 72 | 0.0027 |
| Comp. Ex. 1 | $Pd/Al_2O_3$ | 0.15 | 43 | 17 | 27.29 |
| Comp. Ex. 2 | $Pd_{20}Ag_{80}$ | 200 | 83 | 49 | 0.040 |

[1]The activity relates to the total weight of the used catalysts.

As can be seen from the catalytic data compiled in the above table, the ordered Fe—Al-IMCs and ordered Co—Al-IMCs according to the present invention, at much lower catalyst costs, show significantly enhanced selectivity in selective hydrogenations in comparison to conventional catalysts, as exemplified by the selective hydrogenation of acetylene to ethylene in an excess of ethylene. While due to the low costs of the catalysts, the conversion or activity is of no major concern as this can be compensated for by using higher amounts of catalysts, $Fe_4Al_{13}$ and $o\text{-}Co_4Al_{13}$ proved to be significantly more active than their 1:1 counterparts FeAl and CoAl, at comparably high selectivities and are as such particularly preferred catalysts.

The invention claimed is:

1. A process for the selective hydrogenation of at least one unsaturated hydrocarbon compound using a hydrogenation catalyst comprising an ordered intermetallic compound, which is selected from the group consisting of $Fe_4Al_{13}$, orthorhombic $Co_4Al_{13}$, hexagonal $Co_4Al_{13}$, and monoclinic $Co_4Al_{13}$.

2. The process according to claim 1, wherein the at least one unsaturated hydrocarbon compound has carbon-carbon double and/or triple bond(s) but no other hydrogenable group(s).

3. The process according to claim 1, wherein the at least one unsaturated hydrocarbon compound is selected from the group consisting of alkadienes, cycloalkadienes, alkynes and aryls.

4. The process according to claim 3, wherein the at least one unsaturated hydrocarbon compound is an alkyne, which has 1 to 4 carbon-carbon triple bonds.

5. The process according to claim 4, wherein the at least one unsaturated hydrocarbon is ethyne which is converted to ethene through the hydrogenation.

6. The process according to claim 5, wherein the ethyne is present in admixture with an excess of ethene.

7. The process according to claim 1, wherein the ordered intermetallic compound is a binary cobalt-aluminum intermetallic compound selected from the group consisting of orthorhombic $Co_4Al_{13}$, hexagonal $Co_4Al_{13}$ and monoclinic $Co_4Al_{13}$.

8. The process according to claim 1, wherein the ordered intermetallic compound is a binary iron-aluminum intermetallic which is $Fe_4Al_{13}$.

9. The process according to claim 1, wherein the ordered intermetallic compound is $Fe_4Al_{13}$ or orthorhombic $CO_4Al_{13}$.

10. The process according to claim 1, wherein the ordered intermetallic compound is used as a hydrogenation catalyst in the hydrogenation
   (i) in comminuted form, and/or
   (ii) in the form of a monolith.

11. The process according to claim 10, wherein the ordered intermetallic compound is used in comminuted form in admixture with an inert material.

12. The process according to claim 2, wherein the at least one unsaturated hydrocarbon compound is selected from the group consisting of alkadienes, cycloalkadienes, alkynes and aryls.

* * * * *